United States Patent [19]

Bovenberg et al.

[11] Patent Number: 5,795,733
[45] Date of Patent: Aug. 18, 1998

[54] PROCESS FOR THE EFFICIENT PRODUCTION OF 7-ADCA VIA 3-(CARBOXYETHYLTHIO) PROPIONYL-7-ADCA

[75] Inventors: Roelof Ary Lans Bovenberg, Rotterdam; Bertus Pieter Koekman, Schipluiden; Andreas Hoekema, Oegstgeest; Jan Metske Van Der Laan, Breda; Jan Verweij; Erik De Vroom, both of Leiden, all of Netherlands

[73] Assignee: Gist-Brocades, B.V., Delft, Netherlands

[21] Appl. No.: 591,501

[22] PCT Filed: Jul. 29, 1994

[86] PCT No.: PCT/EP94/02544

§ 371 Date: May 13, 1996

§ 102(e) Date: May 13, 1996

[87] PCT Pub. No.: WO95/04149

PCT Pub. Date: Feb. 9, 1995

[30] Foreign Application Priority Data

Jul. 30, 1993 [EP] European Pat. Off. .............. 93202260
Dec. 24, 1993 [EP] European Pat. Off. .............. 93203695

[51] Int. Cl.$^6$ .......................... C12P 35/02; C12P 37/02; C12N 1/15
[52] U.S. Cl. .................. 435/51; 435/46; 435/47; 435/254.5; 435/252.3; 536/23.2; 536/24.1
[58] Field of Search .................. 435/46, 47, 51, 435/254.5, 69.1, 320.1, 252.3; 540/218; 536/23.2, 24.1

[56] References Cited

U.S. PATENT DOCUMENTS 5,070,020 12/1991 Ingolla et al. .................. 435/183

FOREIGN PATENT DOCUMENTS

| 0 366 354 | 5/1990 | European Pat. Off. . |
| 0 532 341 | 3/1993 | European Pat. Off. . |
| 0 540 210 | 5/1993 | European Pat. Off. . |

OTHER PUBLICATIONS

Baldwin, J. et al., *Tetrahedron*, vol. 43, No. 13, pp. 3009–3014 (1987).
Ballio, A. et al., *Nature*, vol. 185, pp. 97–99 (1960).
Coque, J.J. R. et al., *Molecular and General Genetics*, vol. 236, pp. 453–458 (1993).
Müller et al (1992) Bioc Biop Acta 1116:210–213. "Involvement of Microbodies in Penicillin Biosynthesis".
Maeda et al (1995) Enz. Microb. Tech. 17:231–234 The Substrate Specificity of Deacetoxycephalosporin C Synthase ("Expanse").
Bowers et al (1984) Bioc. Biophys. Res. Comm. 120:607–613 "Enzymatic Synthesis of the Penicilln and Cephalosporin . . . ".

*Primary Examiner*—Keith D. Hendricks
*Attorney, Agent, or Firm*—Morrison and Foerster LLP

[57] ABSTRACT

An overall efficient process for the preparation and recovery of 7-aminodesacetoxycephalosporanic acid (7-ADCA) via 3-(carboxyethylthio)propionyl-7-ADCA, using a *Penicillium chrysogenum* transformant strain expressing expandase in conjunction with acyltransferase, is provided.

15 Claims, 8 Drawing Sheets

```
  1  ATGACGGACGCGACCGTGCCGACCTTCGATCTGGCCGAGCTGCGTGAGGGCTTGCACCAG
  1  ATGACGGACGCGACCGTGCCGACCTTCGATCTGGCCGAGCTGCGTGAGGGCTTGCACCAG

61  GAGGAGTTCCGCCACTGCCTGCGCGAGAAGGGCGTGTTCTACCTCAAGGGCACCGGGCT
 61  GAGGAGTTCCGCCACTGCCTGCGCGAGAAGGGCGTGTTCTACCTCAAGGGCACCGGGCTG
                                                                *

120  C G CCGAGGCGGACCACGCCTCGGCGCGGGAGATCGCGGTGGACTTCTTCGACCACGGC
121  CCGGCCGAGGCGGACCACGCCTCGGGCCGGGAGATCGCGGTGGACTTCTTCGACCACGGC
     * *                      **

178  ACCGAGGCCGAGAAGAAGGCGGTGATGACGCCGATCCCGACCATCCGGCGCGGGTACGCC
181  ACCGAGGCCGAGAAGAAGGCGGTGATGACGCCGATCCCGACCATCCGGCGCGGGTACGCC

238  GGGCTGGAGTCCGAGAGCACCGCGCAGATCACGAACACCGGCAAGTACACCGACTACTCG
241  GGGCTGGAGTCCGAGAGCACCGCGCAGATCACGAACACCGGCAAGTACACCGACTACTCG

298  ATGTCGTACTCGATGGGCACCGCGGACAACCTGTTCCCCAGCGCCGAGTTCGAGAAGGCG
301  ATGTCGTACTCGATGGGCACCGCGGACAACCTGTTCCCCAGCGCCGAGTTCGAGAAGGCG

358  TGGGAGGACTACTTCGCGCGGATGTACCGCGCTTCGCAGGACGTCGCGCGGCAGGTGCTG
361  TGGGAGGACTACTTCGCGCGGATGTACCGCGCTTCGCAGGACGTCGCGCGGCAGGTGCTG

418  ACCTCGGTCGGCGCGGAACCCGAGGTCGGCATGGACGCCTTCCTCGACTGCGAACCCCTG
421  ACCTCGGTCGGCGCGGAACCCGAGGTCGGCATGGACGCCTTCCTCGACTGCGAACCCCTG

478  CTGCGCCTGCGCTACTTCCCCGAGGTGCCCGAGGATCGCGTGGCCGAGGAGCAGCCGCTG
481  CTGCGCCTGCGCTACTTCCCCGAGGTGCCCGAGGATCGCGTGGCCGAGGAGCAGCCGCTG

538  CGGATGGCCCCGCACTACGACCTCTCGATCGTCACCCTGATCCACCAGACCCCTTGCGCG
541  CGGATGGCCCCGCACTACGACCTCTCGATCGTCACCCTGATCCACCAGACCCCTTGCGCG

598  AACGGGTTCGTCAGCCTGCAGGTCGAGGTGGACGGGTCCTATGTGGACATCCCGGCGCAG
601  AACGGGTTCGTCAGCCTGCAGGTCGAGGTGGACGGGTCCTATGTGGACATCCCGGCGCAG

658  CCGGGCGCGGTGCTGGTGTTCTGCGGCGCGGTGGCGACGCTGGTGGCCGACGGCGCGATC
661  CCGGGCGCGGTGCTGGTGTTCTGCGGCGCGGTGGCGACGCTGGTGGCCGACGGCGCGATC

718  AAGGCGCCCAAGCACCACGTGGCCGCGCCCGGCGCGGACAAGCGGGTGGGCAGCAGCCGC
721  AAGGCGCCCAAGCACCACGTGGCCGCGCCCGGCGCGGACAAGCGGGTGGGCAGCAGCCGC

778  ACCTCCAGCGTGTTCTTCCTGCGCCCCAACGGGGACTTCCGCTTCTCGGTGCCGCGGGCC
781  ACCTCCAGCGTGTTCTTCCTGCGCCCCAACGGGGACTTCCGCTTCTCGGTGCCGCGGGCC

838  AGGGAGTGCGGGTTCGACGTCAGCATCCCGGCCGAGACCGCCACCTTCGACGACTGGATC
841  AGGGAGTGCGGGTTCGACGTCAGCATCCCGGCCGAGACCGCCACCTTCGACGACTGGATC

898  GGCGGCAACTACATCAACATCCGGAAGACCGCCGCCGCCCGG    939
901  GGCGGCAACTACATCAACATCCGGAAGACCGCCGCCGCCCGG    942
```

Matches = 937    Length = 942    Matches/length - 99.5 percent

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

GCTGAAGGAG CTGAGCATAT GACGGACGCG ACCGTGCCGA CC    42

( 2 ) INFORMATION FOR SEQ ID NO:2:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

CCCGGGTCTA GATCTAGATC ACCGGGCGGC GGCGGTCTTC CGGATGTT    48

( 2 ) INFORMATION FOR SEQ ID NO:3:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

GATCAGTGAG AGTTGCATAT GGACACGACG GTGCCCACCT TCAGCCTG    48

( 2 ) INFORMATION FOR SEQ ID NO:4:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

CCCGGGTCTA GATCTAGACT ATGCCTTGGA TGTGCGGCGG ATGTT 45

( 2 ) INFORMATION FOR SEQ ID NO:5:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:5:

GAGCTCTGTG AATTCACAGT GACCGGTGAC TCTTTC 36

( 2 ) INFORMATION FOR SEQ ID NO:6:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:6:

GGGAGCCATA TGGATGTCTG CTCAAGCGGG GTAGCT 36

( 2 ) INFORMATION FOR SEQ ID NO:7:

( i ) SEQUENCE CHARACTERISTICS:
      ( A ) LENGTH: 42 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:7:

AGAACGGATT AGTTAGTCTG AATTCAACAA GAACGGCCAG AC 42

( 2 ) INFORMATION FOR SEQ ID NO:8:

( i ) SEQUENCE CHARACTERISTICS:
      ( A ) LENGTH: 42 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:8:

GACAGAGGAT GTGAAGCATA TGTGCTGCGG GTCGGAAGAT GG 42

( 2 ) INFORMATION FOR SEQ ID NO:9:

( i ) SEQUENCE CHARACTERISTICS:
      ( A ) LENGTH: 48 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:9:

ACATCAACAT CCGGAAGACC GCCGCCGCCC GGTGAAGGCT CTTCATGA 48

( 2 ) INFORMATION FOR SEQ ID NO:10:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:10:

GGACTAGTGT CGACCCTGTC CATCCTGAAA GAGTTG                                    36

( 2 ) INFORMATION FOR SEQ ID NO:11:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

ACATCAACAT CCGGAAGACC GCCGCCGCCC GGCTTTGAAG GCTCTTCA                       48

( 2 ) INFORMATION FOR SEQ ID NO:12:

( i ) SEQUENCE CHARACTERISTICS:
        ( A ) LENGTH: 105 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

TTCGATGTCA GCCTGGACGG CGAGACCGCC ACGTTCCAGG ATTGGATCGG GGGCAACTAC          60

GTGAACATCC GCCGCACATC CAAGGCATGA AGGCTCTTCA TGACG                         105

( 2 ) INFORMATION FOR SEQ ID NO:13:

( i ) SEQUENCE CHARACTERISTICS:
        ( A ) LENGTH: 102 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

GATGTCAGCC TGGACGGCGA GACCGCCACG TTCCAGGATT GGATCGGGGG CAACTACGTG          60

AACATCCGCC GCACATCCAA GCTATGAAGG CTCTTCATGA CG                            102

( 2 ) INFORMATION FOR SEQ ID NO:14:

( i ) SEQUENCE CHARACTERISTICS:
        ( A ) LENGTH: 942 base pairs
        ( B ) TYPE: nucleic acid
        ( C ) STRANDEDNESS: single
        ( D ) TOPOLOGY: linear ( x ) PUBLICATION INFORMATION:
        ( A ) AUTHORS: COQUE et al.,
        ( C ) JOURNAL: Mol. Gen. Genet.
        ( D ) VOLUME: 236
        ( F ) PAGES: 453-458
        ( G ) DATE: 1993
        ( K ) RELEVANT RESIDUES IN SEQ ID NO:14: FROM 1 TO 942

( x i ) SEQUENCE DESCRIPTION: SEQ ID NO:14:

ATGACGGACG CGACCGTGCC GACCTTCGAT CTGGCCGAGC TGCGTGAGGG CTTGCACCAG          60

GAGGAGTTCC GCCACTGCCT GCGCGAGAAG GGCGTGTTCT ACCTCAAGGG CACCGGGCTG         120

CCGGCCGAGG CGGACCACGC CTCGGGCCGG GAGATCGCGG TGGACTTCTT CGACCACGGC         180

ACCGAGGCCG AGAAGAAGGC GGTGATGACG CCGATCCCGA CCATCCGGCG CGGGTACGCC         240

GGGCTGGAGT CCGAGAGCAC CGCGCAGATC ACGAACACCG GCAAGTACAC CGACTACTCG         300

ATGTCGTACT CGATGGGCAC CGCGGACAAC CTGTTCCCCA GCGCCGAGTT CGAGAAGGCG         360

TGGGAGGACT ACTTCGCGCG GATGTACCGC GCTTCGCAGG ACGTCGCGCG GCAGGTGCTG         420

ACCTCGGTCG GCGCGGAACC CGAGGTCGGC ATGGACGCCT TCCTCGACTG CGAACCCCTG         480

```
CTGCGCCTGC  GCTACTTCCC  CGAGGTGCCC  GAGGATCGCG  TGGCCGAGGA  GCAGCCGCTG      540

CGGATGGCCC  CGCACTACGA  CCTCTCGATC  GTCACCCTGA  TCCACCAGAC  CCCTTGCGCG      600

AACGGGTTCG  TCAGCCTGCA  GGTCGAGGTG  GACGGGTCCT  ATGTGGACAT  CCCGGCGCAG      660

CCGGGCGCGG  TGCTGGTGTT  CTGCGGCGCG  GTGGCGACGC  TGGTGGCCGA  CGGCGCGATC      720

AAGGCGCCCA  AGCACCACGT  GGCCGCGCCC  GGCGCGGACA  AGCGGGTGGG  CAGCAGCCGC      780

ACCTCCAGCG  TGTTCTTCCT  GCGCCCCAAC  GGGGACTTCC  GCTTCTCGGT  GCCGCGGGCC      840

AGGGAGTGCG  GGTTCGACGT  CAGCATCCCG  GCCGAGACCG  CCACCTTCGA  CGACTGGATC      900

GGCGGCAACT  ACATCAACAT  CCGGAAGACC  GCCGCCGCCC  GG                         942
```

( 2 ) INFORMATION FOR SEQ ID NO:15:

( i ) SEQUENCE CHARACTERISTICS:
        ( A ) LENGTH: 939 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

```
ATGACGGACG  CGACCGTGCC  GACCTTCGAT  CTGGCCGAGC  TGCGTGAGGG  CTTGCACCAG      60

GAGGAGTTCC  GCCACTGCCT  GCGCGAGAAG  GGCGTGTTCT  ACCTCAAGGG  CACCGGGCTC      120

GCCGAGGCGG  ACCACGCCTC  GGCGCGGGAG  ATCGCGGTGG  ACTTCTTCGA  CCACGGCACC      180

GAGGCCGAGA  AGAAGGCGGT  GATGACGCCG  ATCCCGACCA  TCCGGCGCGG  GTACGCCGGG      240

CTGGAGTCCG  AGAGCACCGC  GCAGATCACG  AACACCGGCA  AGTACACCGA  CTACTCGATG      300

TCGTACTCGA  TGGGCACCGC  GGACAACCTG  TTCCCCAGCG  CCGAGTTCGA  GAAGGCGTGG      360

GAGGACTACT  TCGCGCGGAT  GTACCGCGCT  TCGCAGGACG  TCGCGCGGCA  GGTGCTGACC      420

TCGGTCGGCG  CGGAACCCGA  GGTCGGCATG  GACGCCTTCC  TCGACTGCGA  ACCCCTGCTG      480

CGCCTGCGCT  ACTTCCCCGA  GGTGCCCGAG  GATCGCGTGG  CCGAGGAGCA  GCCGCTGCGG      540

ATGGCCCCGC  ACTACGACCT  CTCGATCGTC  ACCCTGATCC  ACCAGACCCC  TTGCGCGAAC      600

GGGTTCGTCA  GCCTGCAGGT  CGAGGTGGAC  GGGTCCTATG  TGGACATCCC  GGCGCAGCCG      660

GGCGCGGTGC  TGGTGTTCTG  CGGCGCGGTG  GCGACGCTGG  TGGCCGACGG  CGCGATCAAG      720

GCGCCCAAGC  ACCACGTGGC  CGCGCCCGGC  GCGGACAAGC  GGGTGGGCAG  CAGCCGCACC      780

TCCAGCGTGT  TCTTCCTGCG  CCCCAACGGG  GACTTCCGCT  TCTCGGTGCC  GCGGGCCAGG      840

GAGTGCGGGT  TCGACGTCAG  CATCCCGGCC  GAGACCGCCA  CCTTCGACGA  CTGGATCGGC      900

GGCAACTACA  TCAACATCCG  GAAGACCGCC  GCCGCCCGG                              939
```

PROCESS FOR THE EFFICIENT PRODUCTION OF 7-ADCA VIA 3-(CARBOXYETHYLTHIO) PROPIONYL-7-ADCA

FIELD OF THE INVENTION AND BRIEF DESCRIPTION OF THE PRIOR ART

The present invention concerns a biosynthetic process for preparation and recovery of 7-aminodesacetoxycephalosporanic acid (7-ADCA).

β-Lactam antibiotics constitute the most important group of antibiotic compounds, with a long history of clinical use. Among this group, the prominent ones are the penicillins and cephalosporins. These compounds are naturally produced by the filamentous fungi *Penicillium chrysogenum* and *Acremonium chrysogenum*, respectively.

As a result of classical strain improvement techniques, the production levels of the antibiotics in *Penicillium chrysogenum* and *Acremonium chrysogenum* have increased dramatically over the past decades. With the increasing knowledge of the biosynthetic pathways leading to penicillins and cephalosporins, and the advent of recombinant DNA technology, new tools for the improvement of production strains and for the in vivo derivatization of the compounds have become available.

Most enzymes involved in β-lactam biosynthesis have been identified and their corresponding genes been cloned, as can be found in Ingolia and Queener, Med. Res. Rev. 9 (1989), 245–264 (biosynthesis route and enzymes), and Aharonowitz, Cohen, and Martin, Ann. Rev. Microbiol. 46 (1992), 461–495 (gene cloning).

The first two steps in the biosynthesis of penicillin in *P. chrysogenum* are the condensation of the three amino acids L-5-amino-5-carboxypentanoic acid (L-α-aminoadipic acid) (A), L-cysteine (C) and L-valine (V) into the tripeptide LLD-ACV, followed by cyclization of this tripeptide to form isopenicillin N. This compound contains the typical β-lactam structure.

The third step involves the exchange of the hydrophilic side chain of L-5-amino-5-carboxypentanoic acid by a hydrophobic side chain by the action of the enzyme acyltransferase (AT). In the industrial process for penicillin G production the side chain of choice is phenylacetic acid (PA). In EP-A-0532341 the application of an adipate (5-carboxypentanoate) feedstock has been disclosed. The incorporation of this substrate leads to a penicillin derivative with a 5-carboxypentanoyl side chain, viz. 5-carboxypentanoyl-6-aminopenicillanic acid. This incorporation is due to the fact that the acyltransferase has a proven wide substrate specificity (Behrens et al., J. Biol. Chem. 175 (1948), 751–809; Cole, Process. Biochem. 1 (1966), 334–338; Ballio et al., Nature 185 (1960), 97–99). The enzymatic exchange reaction mediated by AT takes place inside a cellular organelle, the microbody, as has been described in EP-A-0448180.

Cephalosporins are much more expensive than penicillins. One reason is that some cephalosporins (e.g. cephalexin) are made from penicillins by a number of chemical conversions. Another reason is that, so far, only cephalosporins with a D-5-amino-5-carboxypentanoyl side chain can be fermented. Cephalosporin C, by far the most important starting material in this respect, is very soluble in water at any pH, thus implying lengthy and costly isolation processes using cumbersome and expensive column technology. Cephalosporin C obtained in this way has to be converted into therapeutically used cephalosporins by a number of chemical and enzymatic conversions.

The intermediate 7-ADCA is currently produced by chemical derivatization of penicillin G. The necessary chemical steps to produce 7-ADCA involve the expansion of the 5-membered penicillin ring structure to a 6-membered cephalosporin ring structure. However, the expandase enzyme from the filamentous bacterium *Streptomyces clavuligerus* can carry out such ring expansions. When introduced into *P. chrysogenum*, it can convert the penicillin ring structure into the cephalosporin ring structure, as described in Cantwell et al. , Proc. R. Soc. Lond. B. 248 (1992), 283–289; and in EP-A-0532341 and EP-A-0540210. The expandase enzyme has been well characterized (EP-A-0366354) both biochemically and functionally, as has its corresponding gene. Both physical maps of the cefE gene (EP-A-0233715), DNA sequence and transformation studies in *P. chrysogenum* with cefE have been described.

Another source for a suitable ring expansion enzyme is the filamentous bacterium *Nocardia lactamdurans* (formerly *Streptomyces lactamdurans*). Both the biochemical properties of the enzyme and the DNA sequence of the gene have been described (Cortes et al., J. Gen. Microbiol. 133 (1987), 3165–3174; and Coque et al., Mol. Gen. Genet. 236 (1993), 453–458, respectively).

More particularly, EP-A-0532341 teaches the in vivo use of the expandase enzyme in *P. chrysogenum*, in combination with a 5-carboxypentanoyl side chain as a feedstock, which is used as a substrate for the acyltransferase enzyme in *P. chrysogenum*. This leads to the formation of 5-carboxypentanoyl-6-APA, which is converted by an expandase enzyme introduced into the *P. chrysogenum* strain to yield 5-carboxypentanoyl-7-ADCA. Finally, the removal of the 5-carboxypentanoyl side chain is suggested, yielding 7-ADCA as a final product. The patent application EP-A-0540210 describes a similar process for the preparation of 7-ACA, including the extra steps of converting the 3-methyl side chain of the ADCA ring into the 3-acetoxymethyl side chain of ACA. However, the aforesaid patent applications do not teach an efficient and economically effective process, because, first of all, the problem of timely expression of the expandase enzyme in the cell concomitant with the expression of the acyltransferase enzyme has not been recognized.

In contrast, the present invention provides an efficient process for producing 7-ADCA in which expandase and acyltransferase are expressed simultaneously.

In addition, the application of a new side chain precursor, viz. 3,3'-thiodipropionic acid, is taught by the present invention. This precursor is very efficiently incorporated by *P. chrysogenum* into the corresponding penicillins, which are to be expanded by the subsequent action of the expandase enzyme.

Furthermore, until now no effective way has been described for recovering the 7-ADCA derivative from the fermentation broth before its deacylation. The present invention provides an effective solvent extraction procedure for the recovery of the 7-ADCA derivative.

By the present invention, an efficient overall process is provided for the preparation of 7-ADCA, comprising reaction steps neither disclosed nor suggested in the prior art so far.

Also, by applying the present invention and analogous to the description given in EP-A-0540210, 7-ACA can be prepared in an efficient overall process in this way.

BRIEF DESCRIPTION OF THE FIGURES

FIG. 8: DNA sequence of *Nocardia lactamdurans* cefE (Coque et al., supra) (lower lines) (SEQ ID NO: 14) alligned with sequence PCR product 1 (upper lines) (SEQ ID NO: 15).

BRIEF DESCRIPTION OF THE SEQUENCE LISTING

Figure 1:
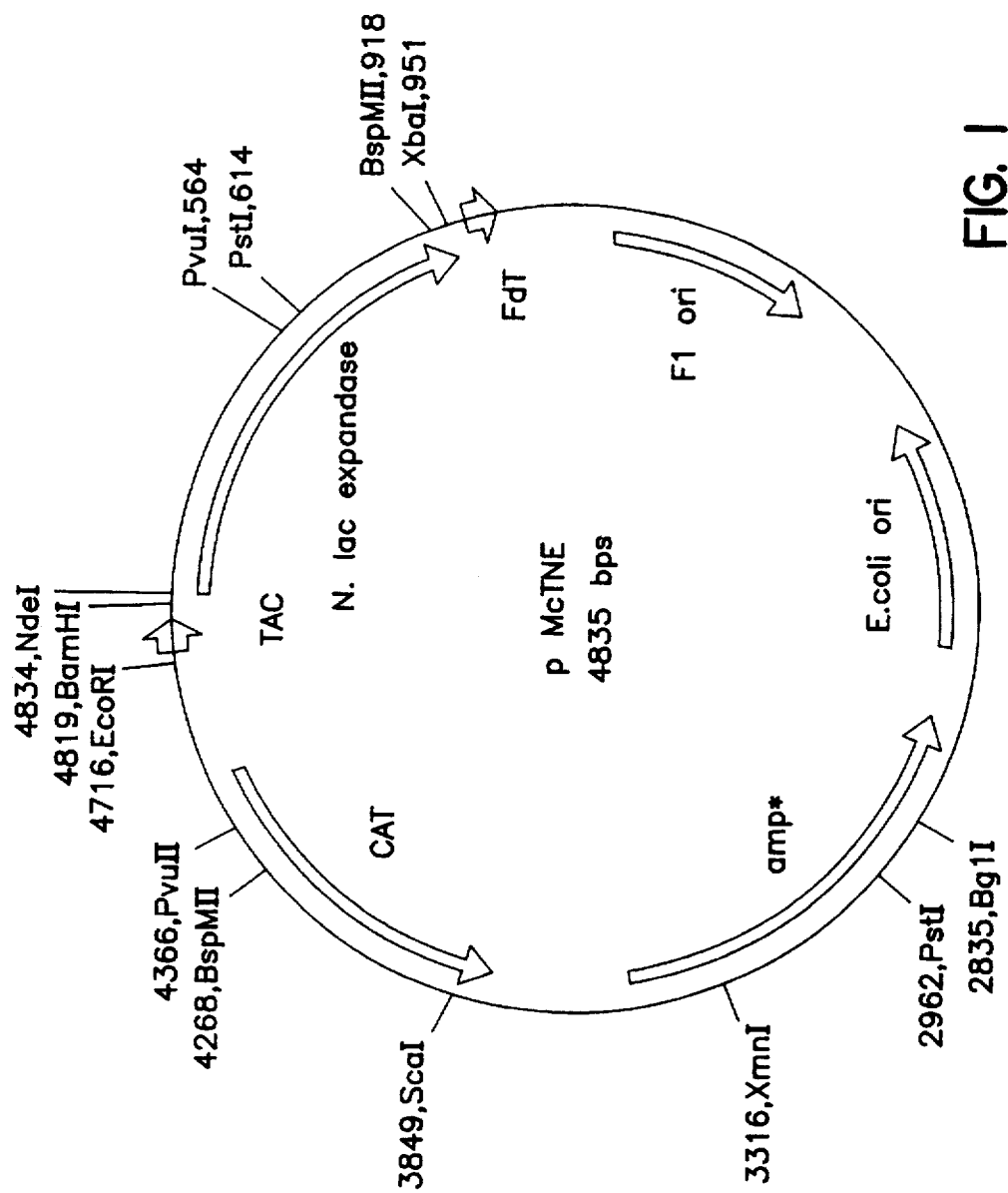
FIG. 1: A functional map of plasmid pMcTNE.

Sequence ID Nos. 1 to 13: oligonucleotides used in the construction of a *P. chrysogenum* expression cassette for the *Streptomyces clavuligerus* and *Nocardia lactamdurans* cefE genes.

Sequence ID No. 16: DNA sequence of *Nocardia lactamdurans* cefE (Coque et al., supra).

SUMMARY OF THE INVENTION

The present invention thus provides a process for the preparation and recovery of 7-aminodesacetoxycephalosporanic acid (7-ADCA) by:

a) transforming a *Penicillium chrysogenum* strain with an expandase gene, under the transcriptional and translational regulation of filamentous fungal expression signals;

b) fermenting said strain in a culture medium and adding to said culture medium 3,3'-thiodipropionic acid or a salt or ester thereof suitable to yield 3-(carboxyethylthio) propionyl-6-aminopenicillanic acid (3-(carboxyethylthio) propionyl-6-APA), which are in situ expanded to form 3-(carboxyethylthio)propionyl-7-ADCA;

c) recovering the 3- (carboxyethylthio) propionyl-7-ADCA from the fermentation broth;

d) deacylating said 3- (carboxyethylthio) propionyl-7-ADCA; and e) recovering the crystalline 7-ADCA.

Preferably, step (e) is a filtration step.

Preferably, the expression of the expandase gene is under the transcriptional and translational regulation of the respective control elements of the AT-gene, providing a simultaneous timing of expression of said genes.

Preferably, 3-(carboxyethylthio)propionyl-7-ADCA is recovered from the fermentation broth by extracting the broth filtrate with an organic solvent immiscible with water at a pH of lower than about 4.5 and back-extracting the same with water at a pH between 4 and 10.

Moreover, a recombinant DNA vector comprising the DNA encoding expandase, functionally linked to the transcriptional and translational control elements of the AT-gene of *P. chrysogenum* or the *A. nidulans* gpdA gene, and host cells transformed with the same, are provided.

DETAILED DESCRIPTION OF THE INVENTION

The present invention concerns the use of functional gene constructs in *P. chrysogenum* for the in vivo expansion of the penicillin ring structure, in combination with the use of a new substrate for the biosynthetic enzymes to form a derivative of a key intermediate in the cephalosporin biosynthesis, 7-aminodesacetoxycephalosporanic acid, or 7-ADCA. This derivative has a chemical composition so as to allow efficient solvent extraction, thus providing an economically attractive recovery process.

Transformation of *P. chrysogenum* can, in principle, be achieved by different means of DNA delivery, like PEG-Ca mediated protoplast uptake, electroporation or particle gun techniques, and selection of transformants. See for example Van den Hondel en Punt, Gene Transfer and Vector Development for-Filamentous Fungi, in: Applied Molecular Genetics of Fungi (Peberdy, Laten, Ogden, Bennett, eds.), Cambridge University Press (1991). The application of dominant and non-dominant selection markers has been described (Van den Hondel, supra). Selection markers of both homologous (*P. chrysogenum* derived) and heterologous (non-*P. chrysogenum* derived) origin have been described.

The application of the different transformant selection markers, homologous or heterologous, in the presence or absence of vector sequences, physically linked or not to the non-selectable DNA, in the selection of transformants are well known.

Preferably a homologous selection marker is used to select transformants of *P. chrysogenum* to limit the amount of heterologous DNA introduced into *P. chrysogenum*. Most preferably a dominant selection marker is used which can be selectively removed from the transformed strain, e.g. the amdS gene of *A. nidulans* or other filamentous fungi (European patent application No. 94201896.1). These preferred characteristics of the *P. chrysogenum* transformant selection marker are very beneficial in process and product registration procedures since no antibiotic resistance markers are involved in the process or will be introduced into the environment.

The most preferred embodiment, the amdS selection marker which can be selectively removed from the strain, allows repeated rounds of transformation using the same dominant selection over and over again. This selection-marker free feature of the novel expandase expressing *P. chrysogenum* strains is crucial for the rapid development of high-producing strains in an industrial strain improvement programme.

The ring-expansion reaction, mediated by the expandase enzyme is introduced into and expressed in this way in *P. chrysogenum*, for instance in strain Wisconsin 54-1255. This ring-expansion reaction is also carried out in mutants thereof having an improved β-lactam yield. It will be clear that in that case, the medium conditions have to be slightly adapted to obtain an efficient growth.

Furthermore, the cefE gene is placed under the transcriptional and translational control of the respective filamentous fungal gene control elements, preferably derived from *P. chrysogenum* acyltransferase (AT) gene, thus allowing its expression in the optimal time frame, synchronized with the action of the acyltransferase enzyme itself. These measures are crucial for the effectiveness of the ring-expansion reaction on the penicillin molecule.

In addition to synchronised expression of the expandase and acyltransferase encoding genes, intracellular co-localisation of part of the expandase enzymes with acyltransferase in microbodies (the intracellular location of acyltransferase) might be advantageous for the development of an economical production process. These preferred embodiments will contribute enormously to reduce the amount of penicillin by-products, which are not tolerated in the 7-ADCA end product by regulatory authorities.

In summary, the present invention teaches how the activity of an expandase enzyme introduced into *P. chrysogenum* can be dedicated to the ring expansion of the penicillin ring in terms of synchronized expression.

In accordance with this invention β-lactam intermediates 3-(carboxyethylthio)propionyl-7-ADCA, are produced in *P. chrysogenum* by adding 3,3'-thiodipropionic acid or a salt or ester thereof. Suitable salts are for instance those of sodium or potassium. The same are efficiently recovered from the media through a simple solvent extraction, for instance, as follows:

The broth is filtered and an organic solvent immiscible with water is added to the filtrate. The pH is adjusted in order to extract the cephalosporin from the aqueous layer. The pH range has to be lower than 4.5; preferably between 4 and 1, more preferably between 2 and 1. In this way the cephalosporin is separated from many other impurities present in the fermentation broth. Preferably a small volume of organic solvent is used, giving a concentrated solution of the cephalosporin, so achieving reduction of the volumetric flow rates. A second possibility is whole broth extraction at a pH of 4 or lower. Preferably the broth is extracted between 4 and 1 with an organic solvent immiscible with water.

Any solvent that does not interfere with the cephalosporin molecule can be used. Suitable solvents are, for instance, butyl acetate, ethyl acetate, methyl isobutyl, ketone, alcohols like butanol etc.. Preferably 1-butanol or isobutanol are used.

Hereafter the cephalosporin is back extracted with water at a pH between 4 and 10, preferably between 6 and 9. Again the final volume is reduced drastically. The recovery can be carried out at temperatures between 0° and 50° C., and preferably at ambient temperatures.

The aqueous cephalosporin solution thus obtained is treated with a suitable enzyme in order to remove the 3-(carboxyethylthio)propionyl side chain and obtain the desired 7-ADCA.

Preferably, an immobilized enzyme is used, in order to be able to use the enzyme repeatedly. The methodology for the preparation of such particles and the immobilization of the enzymes have been described extensively in EP-A-0222462. The pH of the aqueous solution has a value of, for example pH 4 to pH 9, at which the degradation reaction of cephalosporin is minimized and the desired conversion with the enzyme is optimized. Thus, the enzyme is added to the aqueous cephalosporin solution while maintaining the pH at the appropriate level by, for instance, adding an inorganic base, such as a potassium hydroxide solution, or applying a cation exchange resin. When the reaction is completed the immobilized enzyme is removed by filtration. Another possibility is the application of the immobilized enzyme in a fixed or fluidized bed column, or using the enzyme in solution and removing the products by membrane filtration. Subsequently, the reaction mixture is acidified in the presence of an organic solvent immiscible with water.

Suitable enzymes are, for instance, derived from a Pseudomonas SY77 microorganism having a mutation in one or more of the positions 62, 177, 178 and 179. Also enzymes from other Pseudomonas microorganisms, preferably Pseudomonas SE83, optionally having a mutation in one or more of the positions corresponding to the 62, 177, 178 and 179 positions in Pseudomonas SY77, may be used.

After adjusting the pH to about 0.1 to 1.5, the layers are separated and the pH of the aqueous layer is adjusted to 2 to 5. The crystalline 7-ADCA is then filtered off.

The deacylation can also be carried out chemically as known in the prior art, for instance, via the formation of an iminochloride side chain, by adding phosphorus pentachloride at a temperature of lower than 10° C. and subsequently isobutanol at ambient temperatures or lower.

The following examples are offered by way of illustration and not by way of limitation.

EXAMPLES

Example 1

Expression of the Streptomyces and Nocardia cefE gene in *Penicillium chrysogenum* a. General gene cloning and gene transformation procedures

Common techniques used in gene cloning procedures are used in the present application. These techniques include polymerase chain reactions (PCR), synthetic oligonucleotide synthesis, nucleotide sequence analysis of DNA, enzymatic ligation and restriction of DNA, *E. coli* vector subcloning, transformation, and transformant selection, isolation and purification of DNA, DNA characterization by Southern blot analyses and $^{32}$P labelled probes, $^{32}$p labelling of DNA by random priming. These techniques are all very well known in the art and adequately described in many references. See for example Sambrook et al., Molecular Cloning, a Laboratory Manual, Cold Spring Harbor, U.S.A. (1989), Innes et al., PCR protocols, a Guide to Methods and Applications, Academic Press (1990), and McPherson et al., PCR, a Practical Approach, IRL Press (1991).

General procedures used in transformation of filamentous fungi and transformant selection include preparation of fungal protoplasts, DNA transfer and protoplast regeneration conditions, transformant purification and characterization. These procedures are all known in the art and very well documented in: Finkelstein and Ball (eds.), Biotechnology of Filamentous Fungi, technology and products, Butterworth-Heinemann (1992); Bennett and Lasure (eds.), More Gene Manipulations in Fungi, Academic Press (1991); Turner, in: Pühler (ed.), Biotechnology, second completely revised edition, VCH (1992).

More specific applications of gene cloning and gene transformation technology to *Penicillium chrysogenum* are very well documented in Bennett and Lasure (supra) and Finkelstein and Ball (supra).

Synthetic DNA oligonucleotides are synthesized using a commercial DNA synthesizer (Applied Biosystems, Calif., U.S.A.) according to the instructions of the manufacturer.

PCR is performed using a commercial automatic PCR apparatus (Perkin Elmer, U.S.A.) and Ultma DNA polymerase (Perkin Elmer) according to the instructions of the manufacturer.

The hGC PCR protocol (Dutton et al., Nucleic Acids Res. 21, (No. 12) (1993) 2953–2954) was used to be able to amplify the cefE coding regions of the *N. lactamdurans* and the *S. clavuligerus* chromosomal DNA.

Restriction enzymes and other DNA modification enzymes are from BRL (Md., U.S.A.) and used according to the instructions of the manufacturer.

*E. coli* vector pBluescript® is obtained from Stratagene (Calif., U.S.A.).

Other chemicals used are all analytical grade, obtained from various suppliers.

DNA nucleotide sequence analysis is performed using an automatic DNA sequence analysis apparatus (Applied Biosystems) based upon detection of sequence-specific fluorescent labelling according to the instructions of the manufacturer.

b. Culturing of microorganisms

*Streptomyces clavuligerus* ATCC 27064 is grown in tryptic soy broth (Difco). Chromosomal DNA of this strain is used for isolation of the cefE gene (Kovacevic et al., J. Bacteriol. (1989), 754–760).

*Nocardia lactamdurans* ATCC 27382 is also grown in tryptic soy broth (Difco). Chromosomal DNA of this strain is used for isolation of the cefE gene (Coque et al., supra).

*Penicillium chrysogenum* Wisconsin 54-1255 (ATCC 28089) is grown in complete YPD medium (YPD; 1% yeast extract, 2% peptone, 2% glucose). Chromosomal DNA of this strain is used for the isolation of penDE gene 5' and 3' regulatory regions required for cefE gene expression. *Penicillium chrysogenum* ATCC 28089 is also used as a host for cefE gene transformation experiments. Other strains of *Penicillium chrysogenum*, including mutants of strain Wisconsin 54-1255, having an improved β-lactam yield, are also suitable. Depending on the transformant selection marker used, *P. chrysogenum* strains containing mutations in the pyrG, niaD or facA gene may be used. These mutant strains can be obtained by methods well-known in the art (Cantoral, Bio/Technol. 5 (1987), 494–497; Gouka et al., J. Biotechn. 20 (1991), 189–200; and Gouka et al., Appl. Microbiol. Biotechnol. (1993), 514–519).

Culturing of *P. chrysogenum* for generation of protoplasts used in transformation is also done in YPD-medium.

It is well known in the art that the protoplasting and regeneration procedures may differ slightly depending on the particular strain of *Penicillium chrysogenum* used and the transformant selection procedure applied.

*E. coli* WK6 (Zell and Fritz, EMBO J. 6 (1987), 1809–1815), XL1-Blue (Stratagene) and HB101 (Boyer and Roulland-Dussoix, J. Mol. Biol., 41 (1969), 459; Bolivar and Backman, Messages Enzymol. 68 (1979), 2040) are maintained and cultured by using standard *E. coli* culture media (Sambrook, supra).

c. Construction of cefE expression cassettes

The cefE expression cassettes are listed in Table I, which also explains the nomenclature that has been used for these plasmids.

TABLE I

List of cefE expression cassettes that were constructed

| Plasmid | Promoter | Gene | Microbody targeting | Terminator |
|---|---|---|---|---|
| pMCTSE | tac[1] | S.cla cefE | | FdT |
| pMCTNE | tac | N.lac cefE | | Fdt |
| pGSE | gpd[2] | S.cla cefE | | — |
| pGNE | gpd | N.lac cefE | | — |
| pGNETA | gpd | N.lac cefE | + target | AT[3] |
| pGNEWA | gpd | N.lac cefE | Wt | AT |
| pANETA | AT[4] | N.lac cefE | + target | AT |
| pANEWA | AT | N.lac cefE | Wt | AT |
| pGSETA | gpd | S.cla cefE | + target | AT |
| pGSEWA | gpd | S.cla cefE | Wt | AT |
| pASETA | AT | S.cla cefE | + target | AT |
| pASEWA | AT | S.cla cefE | Wt | AT |

Legends:
[1]tac = trp-lac hybrid promoter
[2]gpd = 5'-end of *A. nidulans* gpdA gene
[3]AT = 3'-end of *P. chrysogenum* penDE gene
[4]AT = 5'-end of *P. chrysogenum* penDE gene Published nucleotide sequences of the *S. clavuligerus* cefE gene (Kovacevic, supra); the *N. lactamdurans* cefE gene (Coque, supra); the *A. nidulans* gpdA gene (Punt et al., Gene 69 (1988), 49–57); and the *P. chrysogenum* penDE gene (Barredo et al., Gene 83 (1989), 291–300; Diez et al., Mol. Gen. Genet. 218 (1989) 572–576) have been used to design synthetic oligonucleotides listed in Table II.

TABLE II

Oligonucleotides used in the construction of a *P. chrysogenum* expression cassettes for the *N. lactamdurans* and the *S. clavuligerus* cefE gene (SEQ ID NO: 1 through SEQ ID NO: 13)

1. 5'-GCT GAA GGA GCT GAG CAT ATG ACG GAC GCG ACC GTG CCG ACC-3'
2. 5'-CCC GGG TCT AGA TCT AGA TCA CCG GGC GGC GGC GGT CTT CCG GAT GTT-3'
3. 5'-GAT CAG TGA GAG TTG CAT ATG GAC ACG ACG GTG CCC ACC TTC AGC CTG-3'
4. 5'-CCC GGG TCT AGA TCT AGA CTA TGC CTT GGA TGT GCG GCG GAT GTT-3'
5. 5'-GAG CTC TGT GAA TTC ACA GTG ACC GGT GAC TCT TTC-3'
6. 5'-GGG AGC CAT ATG GAT GTC TGC TCA AGC GGG GTA GCT-3'
7. 5'-AGA ACG GAT TAG TTA GTC TGA ATT CAA CAA GAA CGG CCA GAC-3'
8. 5'-GAC AGA GGA TGT GAA GCA TAT GTG CTG CGG GTC GGA AGA TGG-3'
9. 5'-ACA TCA ACA TCC GGA AGA CCG CCG CCG CCC GGT GAA GGC TCT TCA TGA-3'
10. 5'-GGA CTA GTG TCG ACC CTG TCC ATC CTG AAA GAG TTG-3'
11. 5'-ACA TCA ACA TCC GGA AGA CCG CCG CCG CCC GGC TTT GAA GGC TCT TCA-3'
12. 5'-TTC GAT GTC AGC CTG GAC GGC GAG ACC GCC ACG TTC CAG GAT TGG ATC GGG GGC AAC TAC GTG AAC ATC CGC CGC ACA TCC AAG GCA TGA AGG CTC TTC ATG ACG-3'
13. 5'-GAT GTC AGC CTG GAC GGC GAG ACC GCC ACG TTC CAG GAT TGG ATC GGG GGC AAC TAC GTG AAC ATC CGC CGC ACA TCC AAG CTA TGA AGG CTC TTC ATG ACG-3' c1. Construction of the *E. coli* cefE expression plasmids pMCTSE and pMCTNE

PCR, 1: *N. lactamdurans* cefE

In a first PCR using chromosomal DNA of *N. lactamdurans* and oligonucleotides 1 and 2, the *N. lactamdurans* cefE open reading frame was obtained as a 0.9 kb PCR product, containing a unique NdeI restriction site at the 5'-end and a unique XbaI site at the 3'-end.

PCR, 2: *S. clavuligerus* cefE

In a second PCR using chromosomal DNA of *S. clavuligerus* and oligonucleotides 3 and 4, the *S. clavuligerus* cefE open reading frame was obtained as a 0.9 kb PCR product, also containing a unique NdeI restriction site at the 5'-end and a unique XbaI restriction site at the 3'-end.

Figure 3:
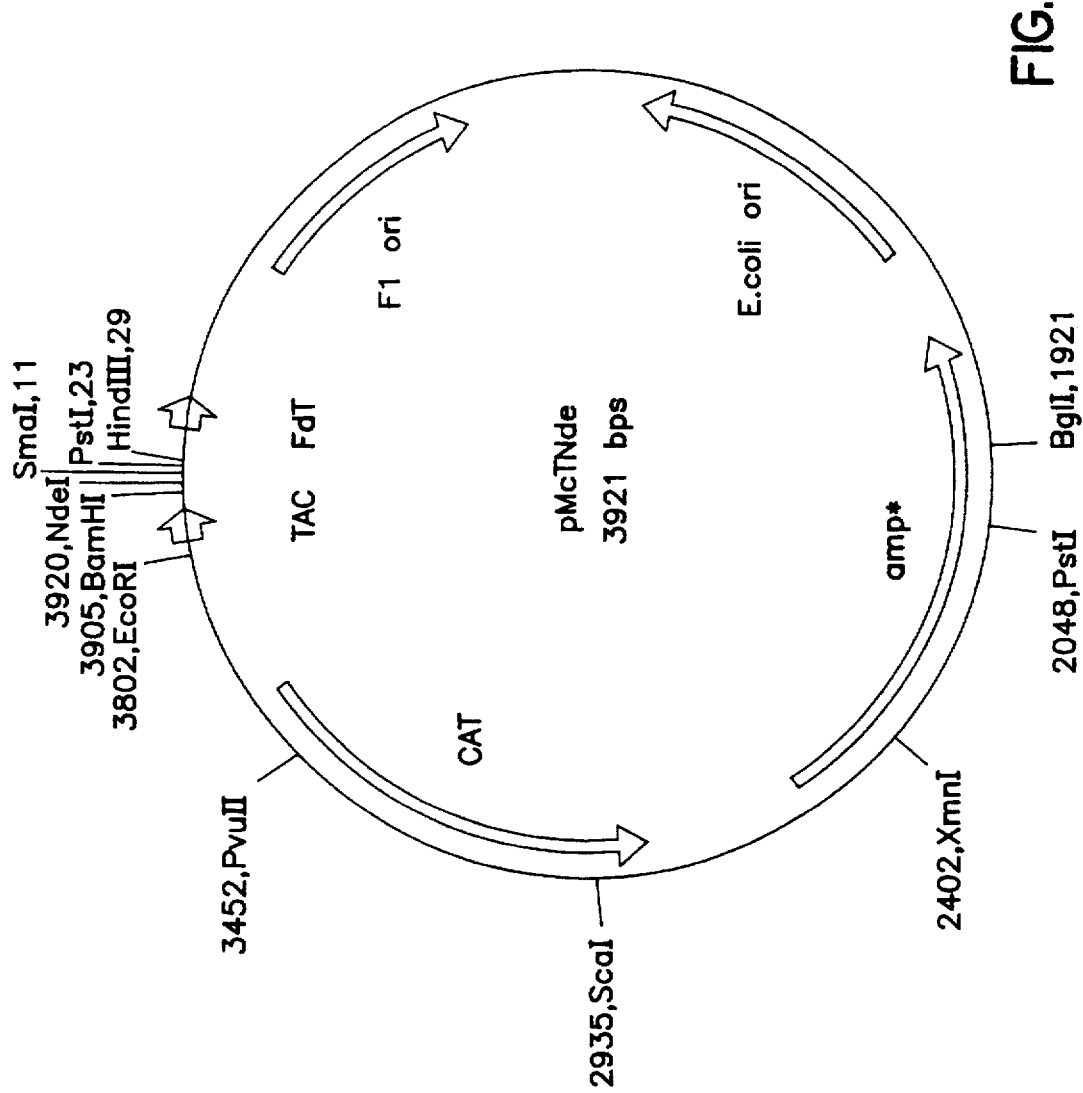
FIG. 3: A functional map of plasmid pMcTNde.

For the purpose of obtaining expression of the cefE genes in *E. coli* and characterisation of the PCR products by DNA sequence analysis, PCR products 1 and 2 were cloned in the vector pMCTNde, a derivative of pMC-5 (Stanssens et al., Nucleic Acids Res. 17 (1989), 4441). Plasmid pMCTNde was derived from pMC5-8 (European patent application No. 0351029) by insertion of a fragment encoding the tac promoter followed by a RBS site and a NdeI cloning site (FIG. 3).

PCR products 1 and 2 were digested with NdeI and XbaI and ligated into NdeI-XbaI digested vector pMCTNde. The ligation mixture was used to transform *E. coli* WK6. Transformants were selected for resistance to chloramphenicol. These transformants are used to isolate plasmid DNA. The cefE expression cassette insert is first analyzed by restriction enzyme digestion on the predicted generation of restriction fragments. Plasmids containing the predicted restriction enzyme sites are finally analyzed by automated DNA sequence analysis.

Figure 2:
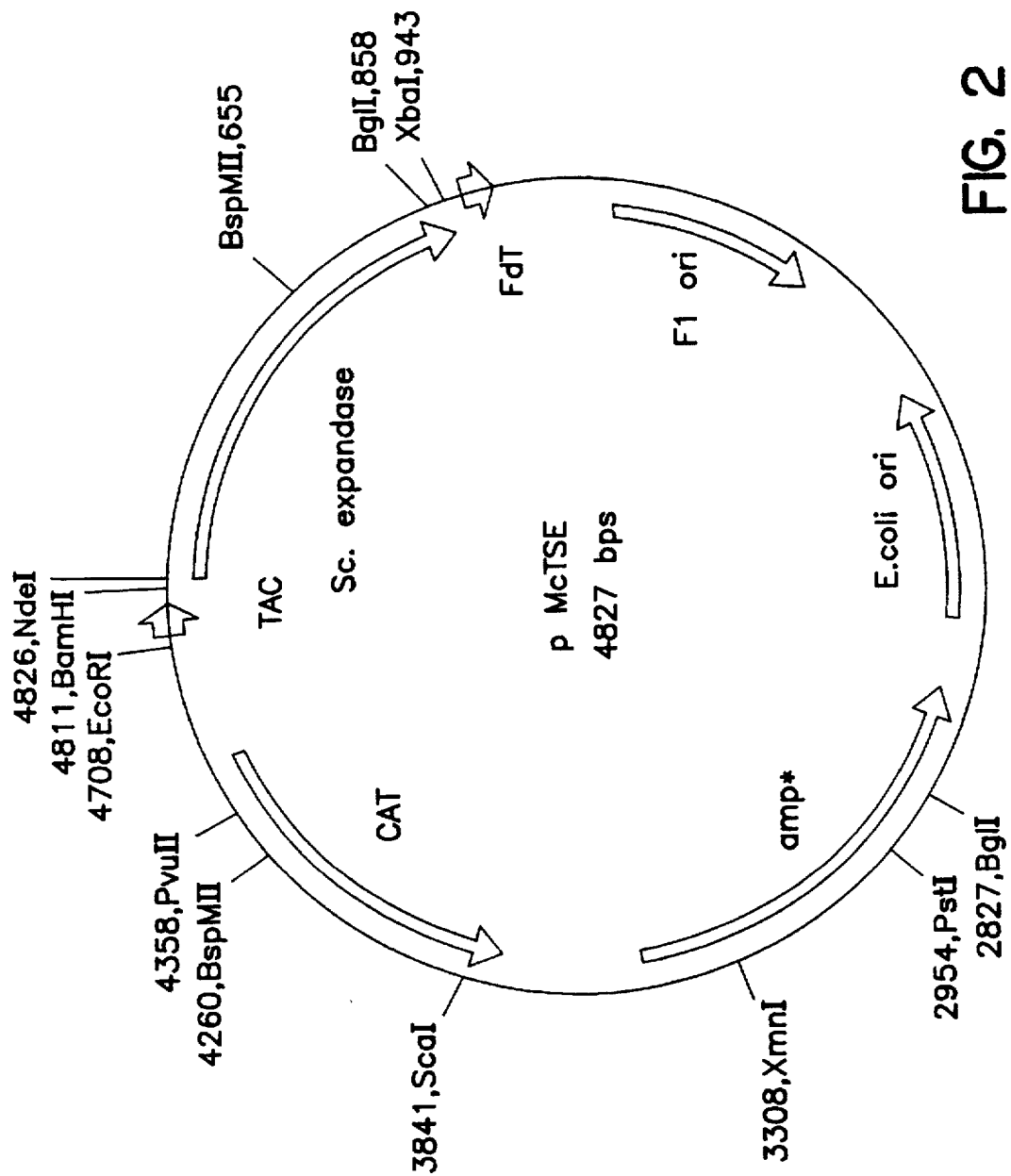
FIG. 2: A functional map of plasmid pMcTSE.

The DNA sequence of the *S. clavuligerus* cefE open reading frame in plasmid pMCTSE (FIG. 2) was 100% identical to the published sequence (Kovacevic, supra).

The DNA sequence (FIG. 8) of all the clones that were analyzed, containing the *N. lactamdurans* cefE open reading frame, was different from the published sequence (Coque, supra).

The derived amino acid sequence of the published *N. lactamdurans* cefE gene has a proline at amino acid position 41 (see Seq.ID No. 16). This proline is missing in the clones that were obtained in PCR 1. This plasmid is called pMCTNE (FIG. 1).

c2. Construction of the *P. chrysogenum* cefE expression plasmids

PCR, 3: gpdA promoter

In this third PCR, using pAN7-1 plasmid DNA (Punt et al. Gene 56 (1987), 117–124), containing the *E. coli* hph gene under control of the *A. nidulans* gpdA promoter and oligonucleotides 5 and 6, the gpdA promoter was obtained as a 0.9 kb PCR product containing a unique EcoRI restriction site at the 5'-end and a unique NdeI site at the 3'-end.

PCR, 4: AT promoter

In the fourth PCR chromosomal DNA of *P. chrysogenum* and oligonucleotides 7 and 8 were used to obtain an AT promoter fragment of 1.5 kb, that also contains a unique EcoRI restriction site at the 5'-end and a unique NdeI site at the 3'-end.

PCR, 5: AT terminator and 3'-end of *N. lactamdurans* cefE gene

In a fifth PCR a 0.5 kb penDE (AT) terminator region was obtained using chromosomal DNA of *P. chrysogenum* and oligonucleotides 9 and 10, and 11 and 10, respectively. These PCR products thus contain the 3'-terminal sequence of the cefE gene with or without a microbody targeting signal, consisting of a C-terminal amino acid sequence ARL (Müller et al., Biochimica et Biophysica Acta 1116 (1992), 210–213).

The oligonucleotides are designed in such a way that a unique BspEI site is introduced at the 5'-end of the PCR product and a unique SpeI site is introduced at the 3'-end of the PCR product.

PCR, 6: AT terminator and 3'-end of *S. clavuligerus* cefE gene

In this sixth PCR the 0.5 kb penDE (AT) terminator region was obtained using chromosomal DNA of *P. chrysogenum* and oligonucleotides 12 and 10, and 13 and 10, respectively. These PCR products thus contain the 3'-terminal sequence of the *S. clavuligerus* cefE gene with or without a microbody targeting signal, consisting of a C-terminal amino acid sequence SKL (De Hoop et al., Biochem. J. 286 (1992), 657–669).

The oligonucleotides are designed in such a way that a unique BglII restriction site is introduced at the 5'-end of the PCR product and a unique SpeI site is obtained at the 3'-end of the PCR product.

For the purpose of obtaining expression of the cefE genes in *P. chrysogenum* the gpdA promoter and the AT promoter fragment were ligated to the cefE fragments from the plasmids pMCTNE and pMCTSE. These ligated fragments were cloned into the vector pBluescript II KS.

PCR 3 was digested with EcoRI and NdeI. pMCTNE and pMCTSE were digested with NdeI and XbaI. The restriction fragments were separated by agarose gel electrophoresis. The 0.9 kb cefE coding fragments were purified from the agarose gel. The EcoRI-NdeI promoter fragment was ligated together with the NdeI-XbaI cefE fragments into EcoRI-XbaI digested vector pBluescript II KS. Thus the following plasmids were obtained: pGSE and pGNE.

To obtain optimal expression of the cefE genes in *P. chrysogenum* we chose to clone the AT termination signal sequence behind the cefE genes in the Penicillium expression plasmids mentioned above.

pGNETA-pGNEWA

Figure 4:
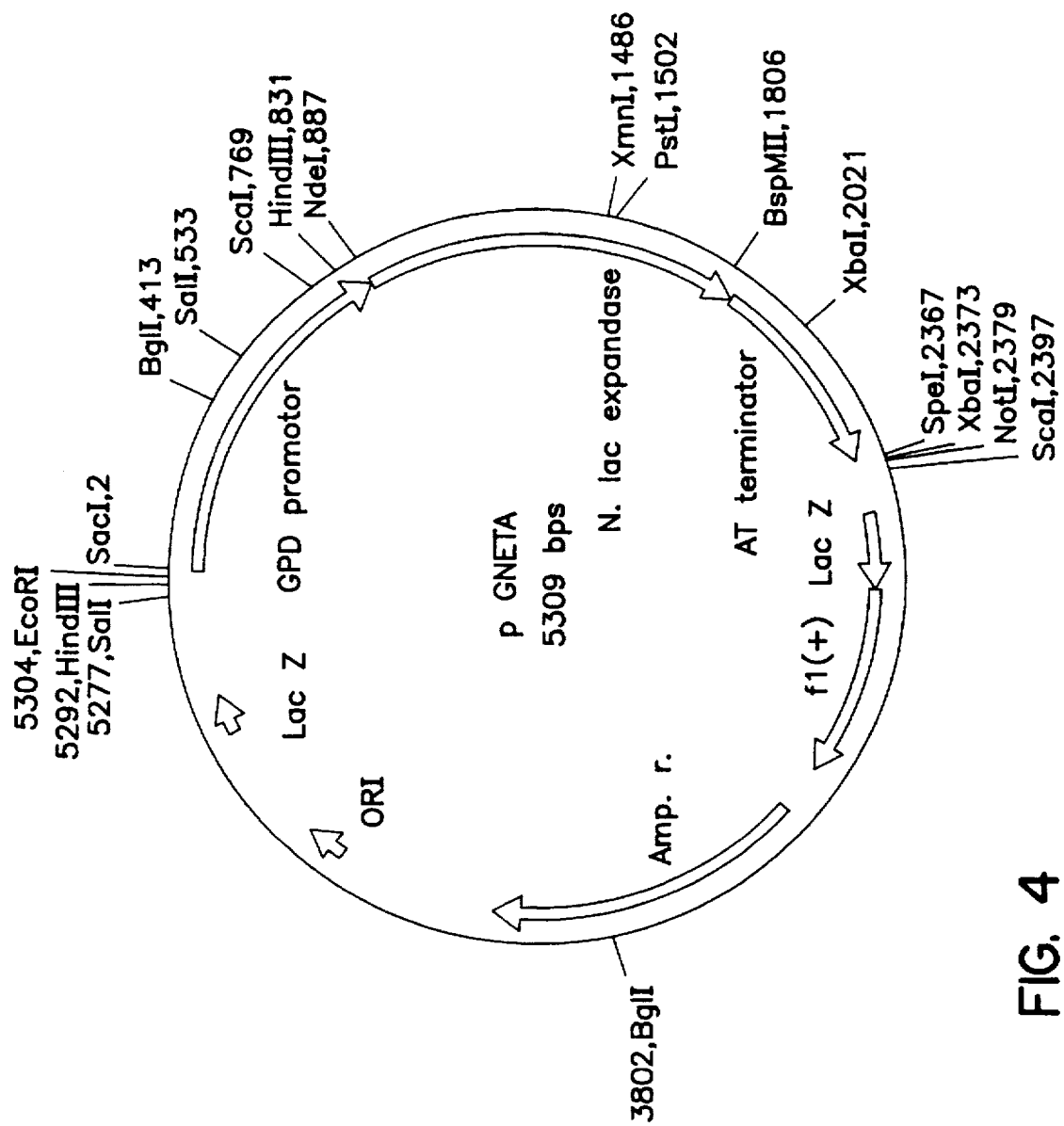
FIG. 4: A functional map of plasmid pGNETA.

PCR 5 products were digested with BspEI and SpeI and ligated into BspEI and SpeI digested vector pGNE. Ligation mixtures were used to transform *E. coli* HB101. Transformants were selected for resistance to ampicillin. Plasmids isolated from these transformants were characterized by restriction fragment analysis and later by DNA sequence analysis. Thus the following plasmids were obtained: pGNEWA and pGNETA (FIG. 4).

pGSETA-pGSEWA

Figure 5:
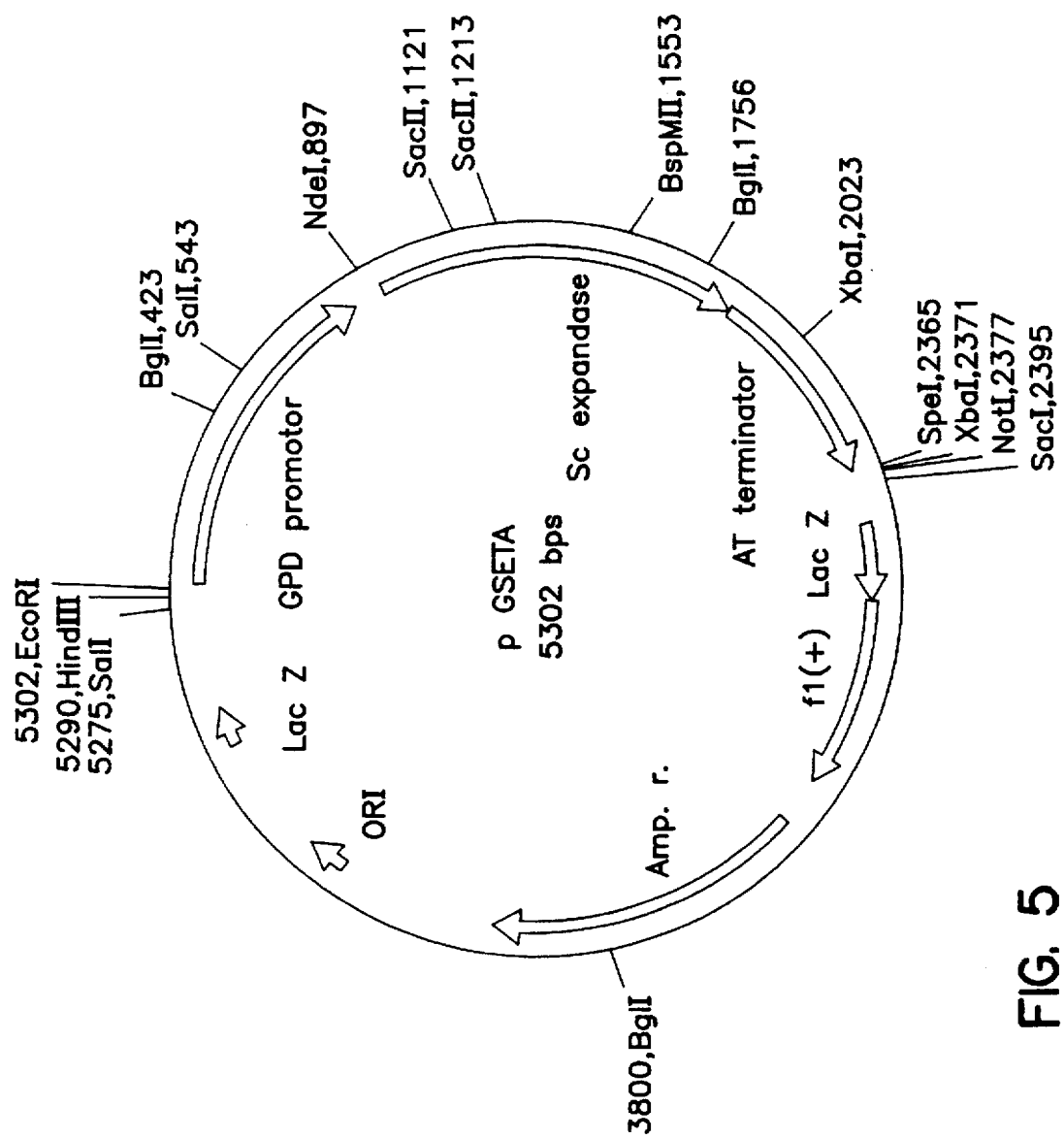
FIG. 5: A functional map of plasmid pGSETA.

PCR 6 products were digested with BalI and SpeI and ligated into BglII and SpeI digested vector pGSE. Ligation mixtures were used to transform *E. coli* HB101. Transformants were selected for resistance to ampicillin. Plasmids isolated from these transformants were also characterized by restriction fragment analysis and later by DNA sequence analysis. Thus the following plasmids were obtained: pGSEWA and pGSETA (FIG. 5).

pANETA, pANEWA and pASETA and pASEWA

The plasmids pGNETA, pGNEWA, pGSETA and pGSEWA were digested with EcoRI and NdeI. The restriction fragments were separated by agarose gel electrophoresis and the 4.5 kb fragments were purified from the gel.

PCR 4 product was digested with EcoRI and NdeI and ligated with the purified fragments mentioned above. After transformation of the ligation mixtures into *E. coli* HB101, transformants were selected for ampicillin resistance.

Figure 6:
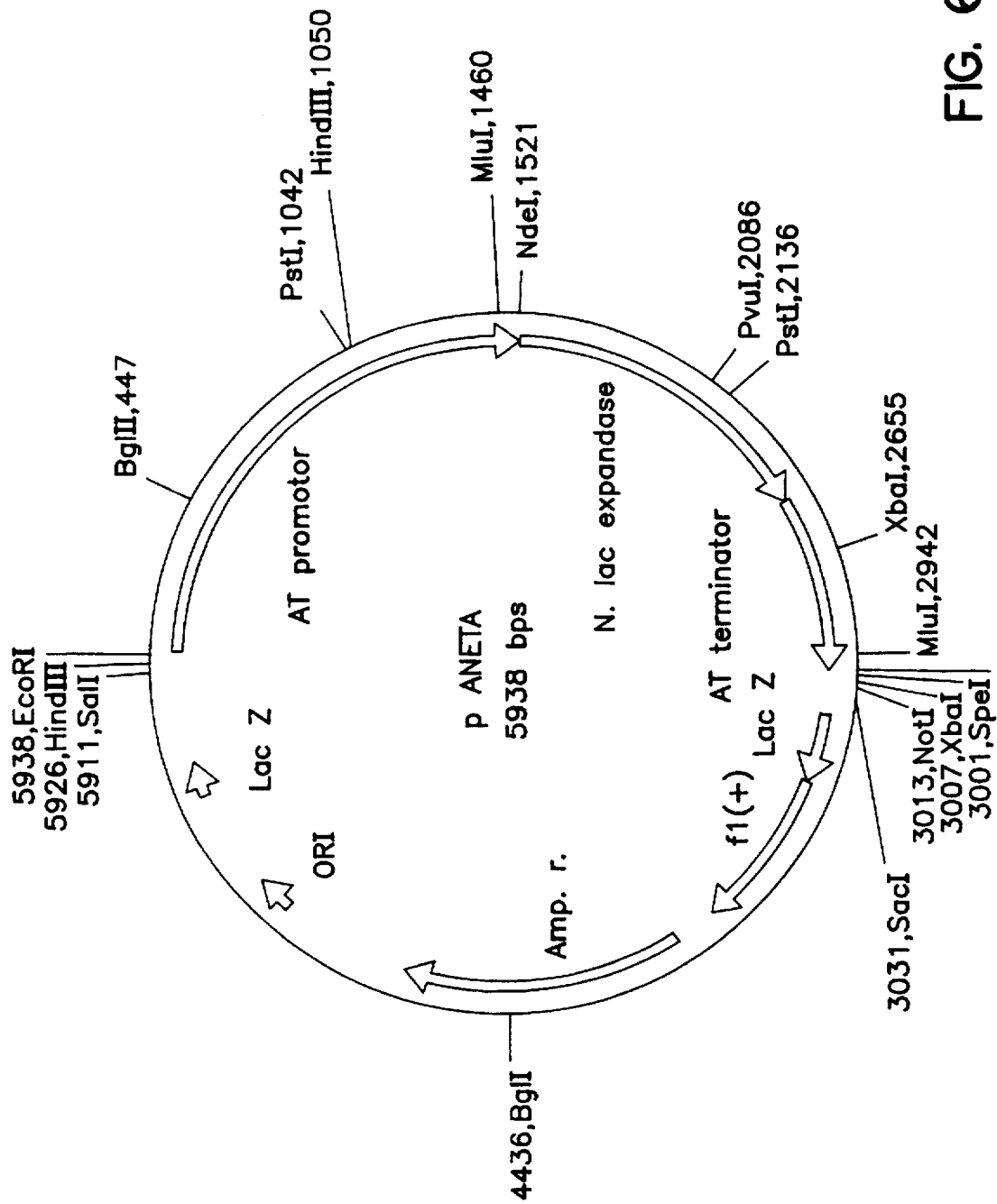
FIG. 6: A functional map-of plasmid pANETA.
Figure 7:
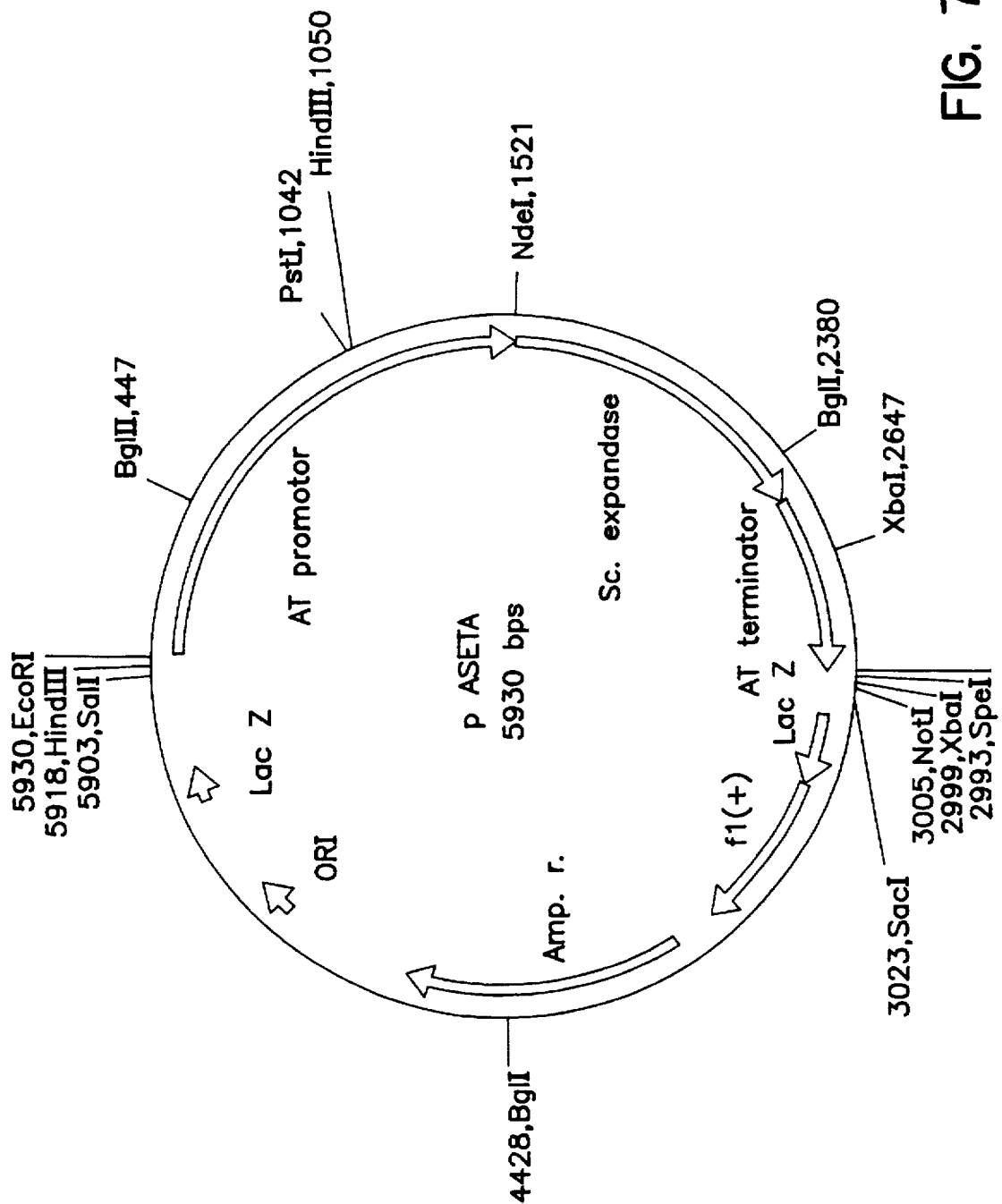
FIG. 7: A functional map of plasmid pASETA.

Transformants were grown and their plasmids were isolated and characterized by restriction fragment analysis and finally DNA sequence analysis. Thus the desired constructs were obtained, viz. pANETA (FIG. 6), pANEWA, pASETA (FIG. 7) and pASEWA.

d. Transformation of *P. chrysogenum*

The Ca-PEG mediated protoplast transformation procedure is used.

Following the procedures described in Cantoral (vide supra), Gouka et al. (J. Biotechn., vide supra) and Gouka et al. (Appl. Microbiol. Biotechnol.,vide supra) total plasmid or the purified cefE expression cassette (devoid of *E. coli* vector sequences) was used to transform strains of *P. chrysogenum* with the pyrG, niaD, facA or amdS (Beri et al., Curr. Genet. 11 (1987), 639–641) genes, respectively, as selection markers.

By using the homologous pyrG, niaD or facA selection markers in purified form, devoid of *E. coli* vector sequences, transformed *P. chrysogenum* strains were obtained which do not contain bacterial resistance genes.

European patent application No. 94201896.1 describes a method for obtaining selection marker gene free recombinant strains. This method was successfully used on *P. chrysogenum* transformants containing the *A. nidulans* amdS gene as a dominant selection marker.

The only elements of heterologous nature then, are the 0.9 kb cefE coding region, and, optionally, the 0.9 kb gpdA promoter region.

e. Analysis of transformants

P. chrysogenum transformants are purified by repeated cultivation on selective medium. Single stable colonies are used to prepare agar slants to produce spores and to screen for transformants containing the cefE expression cassette. Boiling a fragment of fresh mycelium from transformants on an agar plate was used to obtain enough template DNA to efficiently screen hundreds of transformants for the presence of the cefE gene using the PCR technique. (Seth, Fungal Genetics Conference, Asilomar (1991), abstract in Fungal Genetics Newsletter 38, 55.) By doing so efficiency of transformation was estimated.

Screening of transformants was also done using a bioassay. Transformants were grown on agar medium that contained the side-chain precursor of choice. E. coli ESS2231 was used as indicator bacterium in an agar overlay, that also contained Bacto penase to be able to discriminate between penicillin and cephalosporin production according to methods well known in the art and described for example in Guttierez et al., Mol. Gen. Genet. 225 (1991), 56–64)

Spores are used to inoculate P. chrysogenum culture medium as described in section d. After 72 hours of cultivation (at 25° C.) chromosomal DNA is isolated from the mycelium. The DNA is digested with a restriction enzyme with a 6 bp recognition sequence like EcoRI or PstI.

The DNA fragments are separated by agarose gel electrophoresis and blotted onto Gene screen nylon membranes (New England Nuclear). The Southern blots are hybridized with the $^{32}P$ labelled PCR 2 product as a probe for cefE gene sequences. $^{32}P$ labelling of purified PCR 2 product is achieved by random priming labelling in the presence of $\alpha^{32}P$ dCTP by using a commercial labelling kit (Boehringer Mannheim).

Transformants containing the cefE coding sequence are tested for expression of the cefE gene product, here referred to as expandase activity.

Selected transformants are cultivated in penicillin production medium (see Example 2).

In a time-course experiment, mycelium samples are taken after 48, 72 and 96 hours of fermentation. Mycelial extracts are prepared and expandase activity is determined in crude extracts essentially as described in Rollins et al., Can. J. Microbiol. 34 (1988), 1196–1202. Transformants with expandase activity are tested for acyltransferase activity as well by the methods described in Alvarez et al., Antimicrob. Agent Chem. 31 (1987), 1675–1682).

From these analyses transformants with different levels of acyltransferase and expandase enzymatic activities are selected for fermentative production of 7-ADCA derivatives.

Example 2

Fermentative production of 3- (carboxyethylthio) propionyl-7-ADCA and isolation of the same P. chrysogenum strain Wisconsin 54-1255 (ATCC 28089) is transformed with one of the DNA constructs as described in Example 1 and inoculated at 2 * 10$^6$ conidia/ml into a seed medium consisting of (g/l): glucose, 30; $(NH_4)_2SO_4$, 10; $KH_2PO_4$, 10; trace element solution I ($MgSO_4.7H_2O$, 25; $FeSO_4.7H_2O$, 10; $CuSO_4.5H_2O$, 0.5; $ZnSO_4.7H_2$, 2; $Na_2SO_4$, 50; $MnSO_4.H_2O$, 2; $CaCl_2.2H_2O$, 5), 10 (ml/l) (pH before sterilization 6.5).

The seed culture is incubated for 48–72 hours at 25°–30° C. and subsequently used to inoculate 10–20 volumes of a production medium containing (g/l) lactose, 80; maltose, 20; $CaSO_4$, 4; urea, 3; $MgSO_4.7H_2O$, 2; $KH_2PO_4$, 7; NaCl, 0.5; $(NH_4)_2SO_4$, 6; $FeSO_4.7H_2O$; 0.1; 3,3'-thiodipropionic acid, 5; trace element solution II ($CuSO_4.5H_2O$, 0.5; $ZnSO_4.7H_2O$, 2; $MnSO_4.H_2O$, 2; $Na_2SO_4$, 50), 10 (ml/l) (pH before sterilization 5.5–6.0). The incubation is then continued for another 96–120 hours.

At the end of the production fermentation the mycelium is removed by centrifugation or filtration and 3-(carboxyethylthio)propionyl-7-ADCA are analyzed by high performance liquid chromatography (HPLC) on-a reversed-phase column. The HPLC apparatus used is a Beckman System Gold, consisting of a model 126 programmable solvent system, a model 507 autosampler, a model 168 diode-array detector and System Gold data system (5.10). As the stationary phase two (2) Chromspher C18 cartridge columns (100×3 mm, Chrompack) in series are used. The mobile phase consists of a linear gradient from 100% 0.07M phosphate buffer pH 4.8 to 25% acetonitrile and 75% phosphate buffer pH 4.8 in 15 minutes at a flow rate of 0.5 ml/min. The production of 3-(carboxyethylthio)propionyl-7-ADCA is quantitated at 260 nm using synthetic 3-(carboxyethylthio)propionyl-7-ADCA as reference substance.

The peak identity is confirmed by comparison of the on-line UV and NMR spectra.

After filtering of the broth about 0.1 volume of 1-butanol is added to the filtrate. The pH value is adjusted to 2 with diluted hydrochloric acid and the mixture is stirred for 5 minutes at room temperature. After separation, the organic layer is either evaporated and further used in the chemical deacylation (example 3) or back-extracted with 0.33 volume of water of pH 8 and used further in the enzymatic deacylation (example 4).

Example 3

Deacylation of 3-(carboxyethylthio)propionyl-7-ADCA

To a mixture of 3 g (8 mmoles) 3-(carboxyethylthio) propionyl-7-ADCA, 3.5 ml (36 mmoles) of N,N-dimethylaniline, 13 ml of methylene chloride, and 2.6 ml (21 mmoles) of trimethylchlorosilane is added at ambient temperature. After stirring for 30 minutes the reaction mixture is cooled to about −50° C. and 1.8 g (8.5 mmoles) of phosphorus pentachloride is added all at once. The temperature is maintained at −40° C. for two hours and subsequently the reaction mixture is cooled to −65° C. It is then treated with 12 ml (137 mmoles) of isobutanol at such a rate that the temperature does not rise above −40° C. After additional stirring for two hours, the solution is poured in 15 ml of water, and 5 ml of 4.5N ammonia is added immediately afterwards. The pH is adjusted to 4 by slow addition of solid ammonium bicarbonate. After cooling to 5° C. the mixture is filtered, the crystalline 7-ADCA is washed with 5 ml of aqueous acetone (1:1) and isolated.

Example 4

Enzymatic deacylation of 3-(carboxyethylthio)propionyl-7-ADCA using a mutant of Pseudomonas SY77 acylase The conversion of 3-(carboxyethylthio)propionyl-7-ADCA is carried out in a single enzymatic step using a specific acylase which has been derived from Pseudomonas SY77 acylase via region directed mutagenesis. The construction and identification of the mutant Pseudomonas SY77 acylase with improved activity towards the 3-(carboxyethylthio)propionyl side chain has been described in EP-A-0453048. In the mutant the tyrosine at position 178 in the α-subunit of the Pseudomonas SY77 acylase has been replaced by histidine. The mutant acylase is produced in E. coli. Cells are harvested by centrifugation and resuspended in 10 mM phosphate buffer pH 7.4 containing 140 mM NaCl. Subsequently the cells are disrupted by sonification. After removing the cell debris the supernatants containing the acylase activity are collected. Further purification of the acylase is performed by a series of chromatographic steps: (1) ion-exchange chromatography on Q-sepharose fast-flow at pH 8.8; (2) hydrophobic interaction chromatography on Phenyl-Sepharose; and (3) gel-permeation chromatography on a Sephacryl S200HR column.

The purified acylase is immobilized onto particles consisting of a mixture of gelatine and chitosan. The particles are treated with glutaraldehyde just before addition of the enzyme.

The conversion of 3-(carboxyethylthio)propionyl-7-ADCA is carried out in a stirred tank reactor. First the aqueous cephalosporin solution is added to the reactor. Subsequently the temperature of the solution is brought to 30° C. at constant stirring and the pH is fixed at 8 with potassium hydroxide. Then the immobilized enzyme is added and the conversion starts. During the conversion the pH in the reactor is recorded continuously and kept at 8. The 3,3'-thiodipropionic acid which is liberated during the reaction is titrated with KOH. The amount of KOH which is added is integrated and recorded on a flatbed recorder. The conversion is monitored by collecting samples from the reactor which are analyzed for 3-(carboxyethylthio) propionyl-7-ADCA and 7-ADCA by HPLC as described in Example 2.

When the reaction is completed the immobilized enzyme is removed by filtration and the pH of the filtrate is brought to 1 while the filtrate comprises butyl acetate. The layers are separated and the pH of the aqueous phase which contains 7-ADCA is adjusted to 3. The crystalline 7-ADCA is then filtered off.

Example 5

Enzymatic deacylation of 3-(carboxyethylthio)propionyl-7-ADCA using Pseudomonas SE8 acylase The conversion of 3-(carboxyethylthio)propionyl-7-ADCA is carried out as in example 4, however, under the application of Pseudomonas SE83 acylase as acylase, yielding the same result.

---

We claim:

1. A method for making isolated 3-(carboxyethylthio)propionyl-7-aminodesacetoxycephalosporanic acid (3-(carboxyethylthio)propionyl-7-ADCA) comprising the steps of:
   a) culturing a recombinant *Penicillium chrysogenum* strain in a culture medium containing 3,3'-thiodipropionic acid, or a salt or ester thereof;
   b) recovering 3-(carboxyethylthio)propionyl-7-ADCA from the culture medium; wherein said recombinant *Penicillium chrysogenum* strain is altered to contain an expandase gene under the transcriptional and translational regulation of fungal expression signals, and said expandase gene encodes an expandase that can expand 3-(carboxyethylthio)propionyl-6-penicillanic acid (3-(carboxyethylthio)propionyl-6-APA) to 3-(carboxyethylthio)propionyl-7-ADCA.

2. A method according to claim 1, wherein said expression signals are derived from a fungal acyltransferase gene.

3. A method according to claim 1, wherein said expression signals are derived from the acyltransferase gene of *Penicillium chrysogenum*.

4. The method according to claim 1, wherein said expandase gene is derived from *Streptomyces clavuligerus* or *Nocardia lactamdurans*.

5. The method according to claim 2, wherein said expandase gene is derived from *Streptomyces clavuligerus* or *Nocardia lactamdurans*.

6. The method according to claim 3, wherein said expandase gene is derived from *Streptomyces clavuligerus* or *Nocardia lactamdurans*.

7. A process according to claim 1, 2, 3, 4, 5 or 6 wherein said recovery step (b) comprises the steps of:

i) filtering said culture medium and collecting a filtrate;

ii) extracting said filtrate with an organic solvent immiscible with water at a pH lower than about 4.5;

iii) and back-extracting said extracted filtrate with water at a pH between 4 and 10.

8. The method of claim 1, 2, 3, 4 or 5 or 6 further comprising the steps of:

a) deacylating the recovered 3-(carboxyethylthio) propionyl-7-ADCA; and b) recovering 7-ADCA.

9. The method of claim 7, further comprising the steps of:

a) deacylating the recovered 3-(carboxyethylthio) propionyl-7-ADCA; and b) recovering 7-ADCA.

10. The method according to claim 8, wherein said recovery step (b) is by filtration.

11. The method according to claim 9, wherein said recovery step (b) is by filtration.

12. A recombinant DNA vector comprising the DNA encoding expandase, functionally linked to the transcriptional and translational regulation signals of an acyltransferase gene from a filamentous fungus.

13. The vector of claim 12, wherein said DNA encoding expandase is derived from *Streptomyces clavuligerus* or *Nocardia lactamdurans*.

14. A host cell transformed with the vector of claim 12 or 13.

15. The method of claim 10 wherein the recombinant *Penicillium chrysogenum* strain is Wisconsin 54-1255 (ATCC 28089).

* * * * *